(12) United States Patent
Strauss et al.

(10) Patent No.: US 11,485,965 B2
(45) Date of Patent: Nov. 1, 2022

(54) DNA DATA STORAGE ON TWO-DIMENSIONAL SUPPORT MATERIAL

(71) Applicant: MICROSOFT TECHNOLOGY LICENSING, LLC, Redmond, WA (US)

(72) Inventors: Karin Strauss, Seattle, WA (US); Bichlien Hoang Nguyen, Seattle, WA (US); Robert N. Grass, Zurich (CH); Alexander Xavier Christof Kohll, Zurich (CH); Weida Chen, Zurich (CH)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 270 days.

(21) Appl. No.: 16/179,330

(22) Filed: Nov. 2, 2018

(65) Prior Publication Data
US 2020/0140849 A1 May 7, 2020

(51) Int. Cl.
*C12N 15/10* (2006.01)
*C12Q 1/6806* (2018.01)
(Continued)

(52) U.S. Cl.
CPC ....... *C12N 15/1006* (2013.01); *C12Q 1/6806* (2013.01); *C12Q 1/6811* (2013.01);
(Continued)

(58) Field of Classification Search
CPC . C12Q 1/6806; C12Q 1/6811; C12N 15/1006
See application file for complete search history.

(56) References Cited

U.S. PATENT DOCUMENTS

| 2005/0170362 A1* | 8/2005 | Wada ............... G01N 33/5306 435/7.1 |
| 2008/0261045 A1* | 10/2008 | Glass ............... A61K 9/1676 428/403 |
| 2018/0101487 A1* | 4/2018 | Peck .................... C12Q 1/6806 |

FOREIGN PATENT DOCUMENTS

| EP | 2644703 | * | 3/2013 |
| EP | 2644703 A1 | | 10/2013 |
| WO | 2018057526 A2 | | 3/2018 |

OTHER PUBLICATIONS

Reversible DNA encapsulation in silica to produce ROS-resistant and heat-resistant synthetic DNA fossils Daniela Paunescu, Michaela Puddu, Justus OB Soellner, Philipp R Stoessel, Robert N Grass Nature Protocols vol. 8 No. 12 2013 (Year: 2013).*

(Continued)

*Primary Examiner* — Lyle Alexander
*Assistant Examiner* — Dwan A Gerido
(74) *Attorney, Agent, or Firm* — Newport IP, LLC; Benjamin A. Keim

(57) ABSTRACT

A data storage medium is disclosed comprising a two-dimensional (2D) support structure onto which artificially synthesized DNA molecules encoding digital information are placed and then covered with a protective layer. The 2D support structure is formed from a material such as metal foil, glass, or plastic. The 2D support structure may be functionalized with positively charged molecules to improve DNA adhesion. The DNA is protected from degradation by encapsulation in a protective layer of a non-reactive material such as silica or a thin layer of metal. A process for storing DNA on 2D support structures is also disclosed. Correlation of specific DNA molecules with a physical storage location on a 2D support structure provides geometric addressability for selective access to specific digital information.

20 Claims, 7 Drawing Sheets

(51) Int. Cl.
*C12Q 1/6811* (2018.01)
*B82Y 15/00* (2011.01)
*B82Y 30/00* (2011.01)
*B82Y 40/00* (2011.01)

(52) U.S. Cl.
CPC ............... *B82Y 15/00* (2013.01); *B82Y 30/00* (2013.01); *B82Y 40/00* (2013.01)

(56) References Cited

OTHER PUBLICATIONS

Grass, et al., "Robust Chemical Preservation of Digital Information on DNA in Silica with Error-Correcting Codes", In Publication of Angewandte Chemie International Edition, vol. 54, Feb. 16, 2015, pp. 2552-2555.

Ivanova, et al., "Protocols for dry DNA storage and shipment at room temperature", In Molecular Ecology Resources, vol. 13, Sep. 2013, pp. 890-898.

Liu, et al., "Growth of Optically Active Chiral Inorganic Films through DNA Self-Assembly and Silica Mineralisation", In Scientific Reports vol. 4, Article No. 4866, May 2, 2014, pp. 1-7.

Liu, et al., "Template-Assisted Self-Assembly: Alignment, Placement, and Arrangement of Two-Dimensional Mesostructured DNA-Silica Platelets", In Publication of Angewandte Chemie International Edition, vol. 52, Dec. 23, 2013, pp. 14186-14190.

Owens, et al., "Filter Paper for Preservation, Storage, and Distribution of Insect and Pathogen DNA Samples", In Journal of Medical Entomology, vol. 42, No. 4, Jul. 1, 2005, pp. 709-711.

Paunescu, et al., "Reversible DNA encapsulation in silica to produce ROS-resistant and heat-resistant synthetic DNA 'fossils'", In Journal of Nature Protocols, vol. 8, No. 12, Nov. 7, 2013, pp. 2440-2448.

"International Search Report and Written Opinion Issued in PCT Application No. PCT/US19/058414", dated Feb. 7, 2020, 11 Pages.

* cited by examiner

DNA DATA STORAGE ON TWO-DIMENSIONAL SUPPORT MATERIAL

BACKGROUND

The volume of digital information is increasing at an exponential rate. This vast increase in the amount of digital information may outpace the ability of conventional storage technologies. One promising technology for storing large amounts of digital information is deoxyribonucleic acid (DNA). DNA is well known as a molecule that can store genetic information. However, DNA can also function as a storage medium for digital information. Multiple different groups have successfully converted computer files into a string of nucleotide bases, created synthetic DNA encoding that string, sequenced the synthetic DNA, and then recovered the original computer file with 100% accuracy.

As a storage medium, DNA has potential advantages over conventional optical and magnetic media in terms of information densities and stability. Storage using DNA can achieve data density of over 200 petabytes (i.e., 200 million gigabytes) per gram which is much higher than possible with conventional media. With DNA it is possible that all the digital information in the world could be stored in a single room. DNA can also provide better long-term storage. Magnetic and optical media can wear out within five to 10 years. However, readable DNA has been recovered from fossils hundreds of thousands of years old.

Longevity of DNA, however, depends on storage conditions. DNA is susceptible to degradation by heat, enzymes, mutagenic chemicals, and ionizing radiation. When stored in solution, DNA is stable for approximately 10 years, which is the same timescale as other storage media. The ability to access and efficiently retrieve a desired set of digital information also depends on how the DNA is stored. Storage techniques that provide long-term stability and allow efficient access to specified DNA molecules improve the usability of DNA as a storage medium for digital information.

SUMMARY

This disclosure provides structures and methods for stably storing DNA with geometric addressability on a flat, two-dimensional (2D) support material. The DNA is adsorbed to a substrate which provides a structure that may be covered with silica or other protective coating. The 2D surface is a substantially flat surface of an object such as a glass plate, metal sheet, or a plastic sheet. The theoretical maximum density for a single layer of DNA 2 nm thick on a flat, 2D surface is about 340 ng/cm$^2$.

Placement of DNA on the 2D surface at a specific location provides the ability to later locate and retrieve the DNA. For example, a 2D surface such as a sheet of glass may have a specific orientation and the location of DNA on the sheet of glass can be designated by a vertical and horizontal offset from a reference point (e.g., x- and y-coordinates). Digital data storage may use hundreds or thousands of DNA groupings on a single 2D surface. The contents of each DNA grouping may be recorded together with the location on the 2D surface to provide addressability for the DNA in storage. The location record may indicate the identity of DNA molecules and/or the identity of the digital information in a DNA grouping. In an implementation, this identity is stored in association with an identifier of the 2D surface (e.g., a sheet number), an orientation and reference point (e.g., designating which side is the "top" and indicating a particular corner of the surface as the reference point), and offsets relative to the reference point which designate a geometric location for the DNA grouping.

The support material may also be flexible in addition to being flat. The flexible material may be rolled around a spool to provide a structure that is more compact than a ridged, flat sheet. The rolled configuration may be similar in structure to the format of magnetic tape storage media such as a cassette tape or tape reel.

Various steps may be performed to prepare the support material for DNA adsorption. The specific steps depend on the support material. Generally, the support material is functionalized with a positive charge to attract negatively-charged DNA molecules. One technique for functionalizing glass surfaces includes cleaning organic material from the surface with a strong cleaner and then contacting the clean surface with a positively-charged molecule such as an amine bearing silane linker.

DNA density per surface area may be increased by creating multiple layers of DNA on the support material. DNA is a negatively-charged molecule and may be layered together with a polycationic molecule such as a polycationic polymer. As used herein, "polycationic molecule" means a molecule that has three or more separate sites which could potentially be positively charged. In an implementation, the polycationic molecule is polyethyleneimine (PEI). Multiple alternating layers of DNA and the polycationic molecule may be adsorbed to the surface of the support material. Multiple layers of DNA increase the amount of DNA that can be stored on a given amount of surface area as compared to a substrate having only a single layer of DNA.

The DNA adsorbed to the support material is protected from degradation by growing a protective layer over the surface of the DNA. Thus, the DNA is covered with the protective material on one side and protected by the support material on the other side. The protective material is a non-reactive material such as silica. Silica encapsulation may be performed by exposing the DNA to a tetra alkoxysilane such as tetraethyl orthosilicate (TEOS). Exposing the DNA to the silica-containing compound may occur over a prolonged period of time such as multiple hours or days. Encapsulation in silica protects the DNA from DNA degrading agents such as reactive oxygen species or enzymes. Encapsulation in silica may hermetically seal the DNA under glass thereby protecting it from chemical attack, high temperatures, and humidity. This increases the durability of DNA and makes long-term storage of digital information feasible.

Following storage, the DNA may be released from the silica encapsulation by contact with an etching solution such as hydrogen fluoride that dissolves silica without harming the DNA. When a particular grouping of DNA is retrieved from storage, the location record for that DNA is used to identify the location on the 2D surface to apply the etching solution. Controlled application of the etching solution allows for selective retrieval of specific DNA from the 2D surface of the support material while leaving other DNA groupings in place. Once released from encapsulation, the DNA may then be sequenced or otherwise processed. The sequence of nucleotide bases in the DNA may be decoded to obtain the stored digital information.

These structures and techniques described in this disclosure have applications for storing synthetic DNA encoding digital information but are equally suitable for storing naturally occurring DNA in a protected and addressable way.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
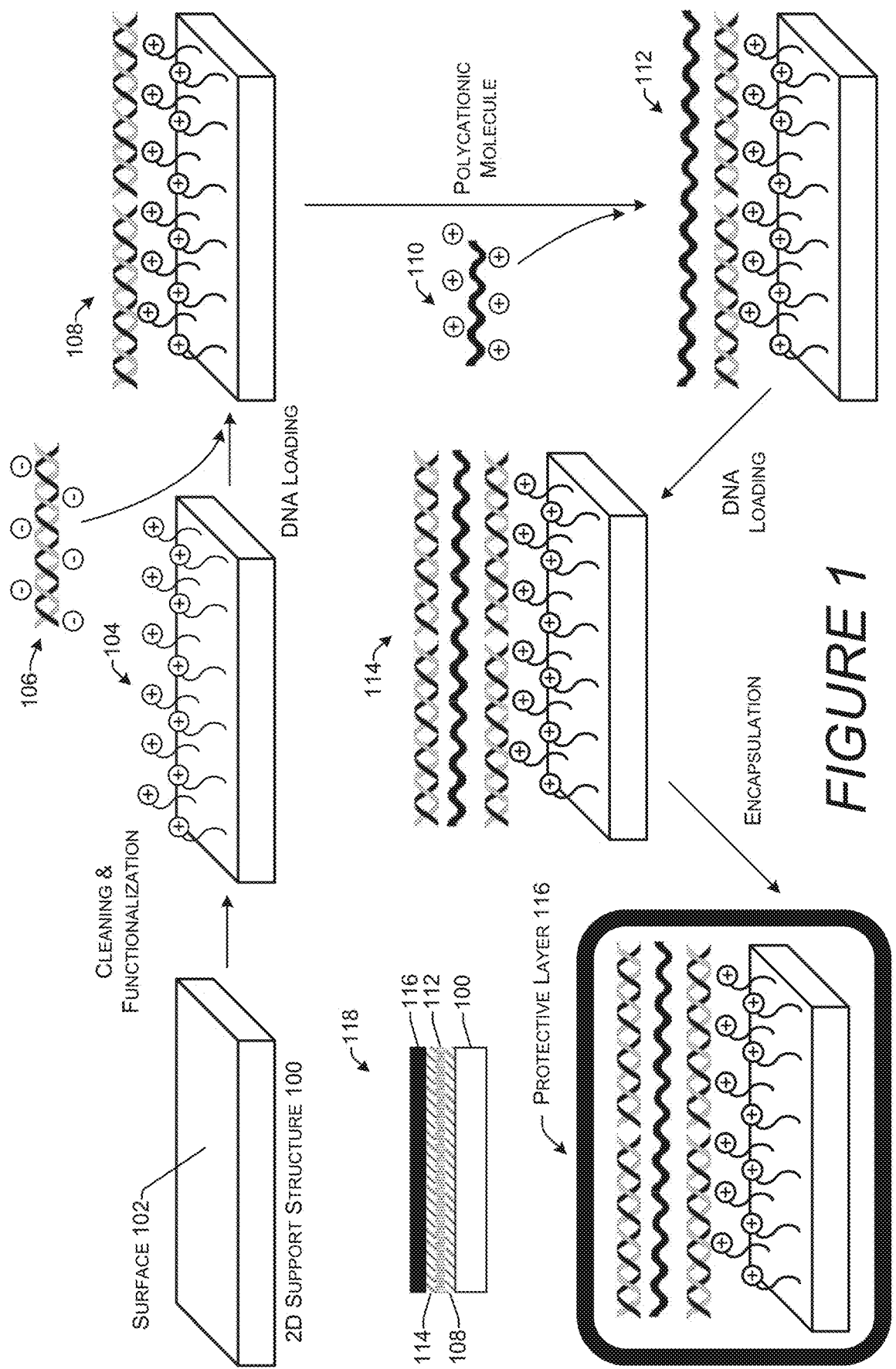
FIG. 1 is a diagram illustrating a structure and process for adsorbing DNA to a 2D support structure and encapsulating the DNA in a protective layer of material.

Polynucleotides such as DNA and ribonucleic acid (RNA), including polynucleotides that have unnatural bases, may be used to store digital information by designing a sequence of nucleotide bases that encodes the zeros and ones of the digital information. There are various techniques and encoding schemes known to those of skill in the art for using nucleotide bases to represent digital information. See e.g., Grass et al., *Robust Chemical Preservation of Digital Information on DNA in Silica with Error-Correcting Codes*, 54 Angew. Chem. Int. Ed. 2552 (2015) and Organick et al., *Random access in large-scale DNA data storage*, 36:3 Nat. Biotech. 243 (2018). Advantages of using DNA rather than another storage media for storing digital information include information density and longevity. The DNA storage structure and methods described in this disclosure can improve information density, longevity, and accessibility relative to other techniques for storing DNA. The contents of the disclosure may be used with any type of polynucleotide such as DNA, RNA, and DNA-RNA hybrids, thus references to "DNA" are illustrative and not intended to limit the application to only DNA or to only use of natural nucleotide bases.

Providing addressable access to DNA in storage while also maintaining stability and high data-density is a challenge. Addressable access or "addressability" refers to the ability to associate specific information with a location on a storage medium to enable selective random access to the information. For example, with magnetic hard disk drives, a specific location may be indicated by a sector and a position in a track of a magnetic platter.

DNA is often stored in a manner that makes accessing a specific subset of the DNA molecules difficult. If DNA is stored in solution, it is difficult to separately access only some of the molecules stored in a container. For example, all the DNA in a buffered solution in an Eppendorf tube must be accessed and processed together. Another technique for storing DNA involves adhering the DNA to the surface of nanoparticles. See, U.S. patent application Ser. No. 16/017,682 entitled "Silica Encapsulated DNA on Magnetic Nanoparticles" filed on Jun. 25, 2018 However, it is difficult to separate specific nanoparticles from a group of nanoparticles stored together. Some level of addressability may be achieved by separating stored DNA into multiple different containers that each include DNA in solution, DNA-coated nanoparticles, or other DNA stored in some other form. However, the containers themselves provide additional volume which reduces data density. There may also be additional processing, purification, or physical manipulation required to access DNA stored within a container, adhered to a nanoparticle, etc.

Storing groupings of DNA at specific locations on a substantially flat, 2D surface provides addressability in a way that minimizes the space consumed because each grouping of DNA does not require its own container. As used herein, "substantially flat" includes perfectly flat surfaces, surfaces that are flat within the limits of the manufacturing tolerances of the method of making the material, and surfaces with minimal curvature such a radius of curvature of less than 1 meter. "Substantially flat" also includes structures that have a locally flat region of at least about one centimeter in diameter even if other portions of the same surface are not flat.

One or more thin sheets of material may be stored in a compact arrangement that provides multiple, substantially flat 2D surfaces on which DNA can be stored. If the thin material is also flexible, it may be rolled around a spool to create a higher density format for storing the DNA. However, DNA molecules applied to a flat material without surface preparation or a protective coating may degrade quickly. Thus, techniques for stably storing DNA on a 2D support surface may include preparation of the surface by functionalization and encapsulation of the DNA with a protective material such as silica.

The term "stably storing" refers to storage conditions that preserve the items stored in an unchanged or substantially unchanged condition for a period of time longer than the item would be unchanged absent the specific storage conditions. In the context of DNA storage, "stably storing" may refer to storing DNA at room temperature and relative humidity (RH) of approximately 50% for greater than 10 years with less than 1% degradation. "Stably storing" may also refer to a technique or structure for storage the reduces degradation of the items stored to a rate that is less than half that of items stored under similar conditions without use of the specific storage technique or structure.

FIG. 1 illustrates a schematic representation of a technique for stably storing DNA on a 2D support structure 100. The 2D support structure 100 has at least one substantially flat surface 102 and is constructed of a material such as glass, a metal foil, or plastic. Suitable types of glass that may be used include, but are not limited to, soda lime glass and borosilicate glass. The metal used in the metal foil may be aluminum, copper, tin, or alloys thereof. The plastic may be formed from a polymer or combination of polymers that create a barrier with low permeability to oxygen and water such as polyvinylidene chloride (PVdC) film, ethylene-vinyl alcohol copolymer (EVOH) film, liquid crystal polymer (LCP) barrier film, and polychlorotrifluoroethylene (PCTFE or PTFCE) film. Polymer composites with reinforcing fillers (e.g., clay nanoparticles, carbon nanotubes, graphene, etc.) integrated in a polymer matrix may also be used as the 2D support structure.

The surface 102 of the 2D support structure 100 may be cleaned and functionalized prior to DNA loading. Cleaning may improve the functionalization of the support surface 102. In an implementation, the cleaning may remove all or substantially all organic material from the surface 102. Cleaning may be performed by application of strong chemicals, plasma cleaning, or another technique. A chemical cleaning solution may be strongly acidic and/or strongly oxidizing. The chemical cleaning solution may include sulfuric acid and/or hydrogen peroxide solution. One type of chemical cleaning solution with this composition is referred to as "piranha solution." Piranha solution includes a mixture of concentrated sulfuric acid and 30% hydrogen peroxide solution at a ratio ranging from 3:1 to 7:1. One commercial source of piranha solution is Nano-Strip® from VWR™ International, LLC (catalog number 10135-756).

Plasma cleaning, another suitable technique for cleaning the surface 102, is the removal of impurities and contaminants from surfaces through the use of an energetic plasma or dielectric barrier discharge (DBD) plasma created from gaseous species. Gases such as argon and oxygen, as well as mixtures such as air and hydrogen/nitrogen are used. The plasma is created by using high-frequency voltages (typically kHz to >MHz) to ionize the low-pressure gas (typically around 1/1000 atmospheric pressure), although atmospheric pressure plasmas are possible. If the gas used is oxygen, the plasma is an effective method for removing organic material. The short-wave ultraviolet energy is effective in the breaking of most organic bonds (i.e., C—H, C—C, C=C, C—O, and C—N) of surface contaminants. If the 2D support structure 100 is an easily oxidized metal, plasma cleaning may be performed with an inert gas such as argon or helium.

The surface 102 may be functionalized to create a functionalized surface layer. Functionalization may add any type of functional group that is capable of attaching positive charged entities 104 to the surface 102. The surface 102 may be functionalized by the use of an amine bearing silane linker. Silanes are saturated chemical compounds consisting of one or multiple silicon atoms linked to each other, or one or multiple atoms of other chemical elements, as the tetrahedral centers of multiple single bonds. One silane that is suitable for functionalizing glass and aluminum is N-Trimethoxysilylpropyl-N,N,N-trimethylammonium abbreviated TMAPS. TMAPS is a tertiary amine. The chloride salt of TMAPS has the formula $C_9H_{24}ClNO_3Si$ and is available in 50% methanol from Fisher Scientific company L.L.C. (catalog number AAH6641414). Functionalization with TMAPS places positively charged entities 104 on the surface 102 creating a positively charged layer. Other positively charged molecules that bind to the surface 102 may be used instead of TMAPS. Another suitable silane is 3-Aminopropyl)triethoxysilane (APTES) which is a primary amine.

The functionalized layer on the surface 102 that includes positive charged entities 104 attracts negatively charged DNA 106 through electrostatic forces. DNA loading may be performed by contacting the functionalized surface 102 with DNA 106. An aqueous solution of DNA 106 may be applied to the surface 102 after functionalization. The length of the DNA 106 may be approximately 80-300 base pairs (bp), approximately 100-200 bp, approximately 120-180 bp, or approximately 150 bp. The DNA 106 may encode digital information. The DNA loading may achieve a density of at least 40 ng/cm$^2$, at least 100 ng/cm$^2$, at least 150 ng/cm$^2$, or at least 180 ng/cm$^2$. In an implementation the loading density may be about 42 ng/cm$^2$ in another implementation the loading density may be about 165 ng/cm$^2$.

Adhesion of multiple strands of DNA 106 creates a DNA layer 108 adhered to the positively charged entities 104. The amount of DNA stored per unit of surface area, and thus the ultimate data density of the storage medium, may in some implementations be increased by placing multiple layers of DNA onto the 2D support structure 100. DNA may be layered onto the 2D support structure 100 by creating alternating layers of polycationic molecules 110 and DNA. The polycationic molecule 110 binds to the DNA layer 108 through electrostatic forces.

The polycationic molecule 110 may be a polycationic linear macromolecule such as polyethyleneimine (PEI), poly-l-lysine (PLL), diethylaminoethyl-dextran (DEAE-dextran), or a branched polymer such as poly(amidoamine) (PAMAM) dendrimers. PEI or polyaziridine is a polymer with repeating units composed of the amine group and two-carbon aliphatic $CH_2CH_2$ spacer. Linear polyethyleneimines contain all secondary amines. PLL is a specific chiral configuration of the synthetic polymer α-polylysine with L-lysine at lysine's central carbon. DEAE-dextran is a positively charged dextran derivative that binds and interacts with negatively-charged DNA molecules and via an unknown mechanism. PAMAM is a class of dendrimer which is made of repetitively branched subunits of amide and amine functionality. PAMAMs have a sphere-like shape overall and are typified by an internal molecular architecture including tree-like branching, with each outward layer, or generation, containing exponentially more branching points. Surface amine residues on PAMAM dendrimers bind to the phosphate backbone of DNA through charged interactions.

Addition of the polycationic molecule 110 creates a positively charged layer 112. Further DNA loading places a second DNA layer 114 on top of the positively charged layer 112. This may be repeated to create two, three, four, or more layers of DNA alternating with positively charged layers 112 formed from polycationic molecules 110. Without being bound by theory, it is believed that the alternating positive and negative charges of the layers creates a stable structure through electrostatic forces.

After the DNA layer 108 and any additional DNA layers such as the second DNA layer 114 are added, the DNA layers 108, 114 may be encapsulated by a protective layer 116. The protective layer 116 may surround the 2D support structure 100 and the DNA layers 108 and 114 as shown in FIG. 1. Alternatively, the protective layer 116 may coat all or part of the surface 102 without fully surrounding the 2D support structure 100. In an implementation, the outermost DNA layer 114 may be covered with a polycationic molecule (either the same or different molecule as the polycationic molecule 110) to create a positively charged layer between the DNA layer 114 and the protective layer 116. A covering layer of polycationic molecules prevents the protectively layer 116 from directly contacting the DNA layer 114 and may provide additional protection for the DNA.

The protective layer 116 is non-porous and protects the DNA layers 108, 114 from air and moisture. One suitable material for the protective layer 116 is silica. Silicon dioxide, also known as silica, silicic acid or silicic acid anhydride is an oxide of silicon with the chemical formula SiO□. A protective layer 116 of silica may be formed by contacting the DNA layers 108, 114 on the 2D support structure 100 with a silica-containing compound such as one or more tetra alkoxysilanes. In an implementation, the tetra alkoxysilane(s) may have an alkoxy chain with between one and five carbon atoms. For example, the tetra alkoxysilane may be tetramethyl orthosilicate, tetraethyl orthosilicate (TEOS), tetrapropyl orthosilicate, tetrabutyl orthosilicate, tetrapentyl orthosilicate, APTES, or mixtures thereof.

In an implementation, the tetra alkoxysilane is TEOS. TEOS is a chemical compound with the formula $Si(OC_2H_5)_4$. TEOS is a colorless liquid that degrades in water. TEOS is the ethyl ester of orthosilicic acid, $Si(OH)_4$. It is the most prevalent alkoxide of silicon. TEOS easily converts to silicon dioxide upon the addition of water. This hydrolysis reaction is an example of a sol-gel process. The side product is ethanol. The reaction proceeds via a series of condensation reactions that convert the TEOS molecule into a mineral-like solid via the formation of Si—O—Si linkages. Rates of this conversion are sensitive to the presence of acids and bases, both of which serve as catalysts.

The silica-containing compound may be present in an aqueous solution and applied to the surface 102 for an extended period of time such as several hours or days. In some implementations, the silica layer formed over the surface 102 by this method may be approximately 10 nm thick. A protective layer 116 of silica may also be formed by sputter deposition of silicon dioxide. Sputter deposition is a physical vapor deposition (PVD) method of depositing thin films by ejecting sputtering material from a "target" that is a source of the material, then depositing it onto a "substrate" which in this application would be the surface 102. Chemical vapor deposition (CVD) may also be used to deposit silica onto the surface 102. CVD is a deposition method used to apply a thin film of solid material to a surface typically under vacuum. For example, with CVD, polycrystalline silicon may be deposited from trichlorosilane ($SiHCl_3$) or silane ($SiH_4$).

Other materials besides silica may be used to form the protective layer 116. For example, metals such as gold or titanium oxide, aluminum oxide may be used to encapsulate and protect the DNA layers 108, 114. Titanium oxide or aluminum oxides may also be deposited by CVD. A protective layer 116 of gold may be formed by PVD.

Figure 2:
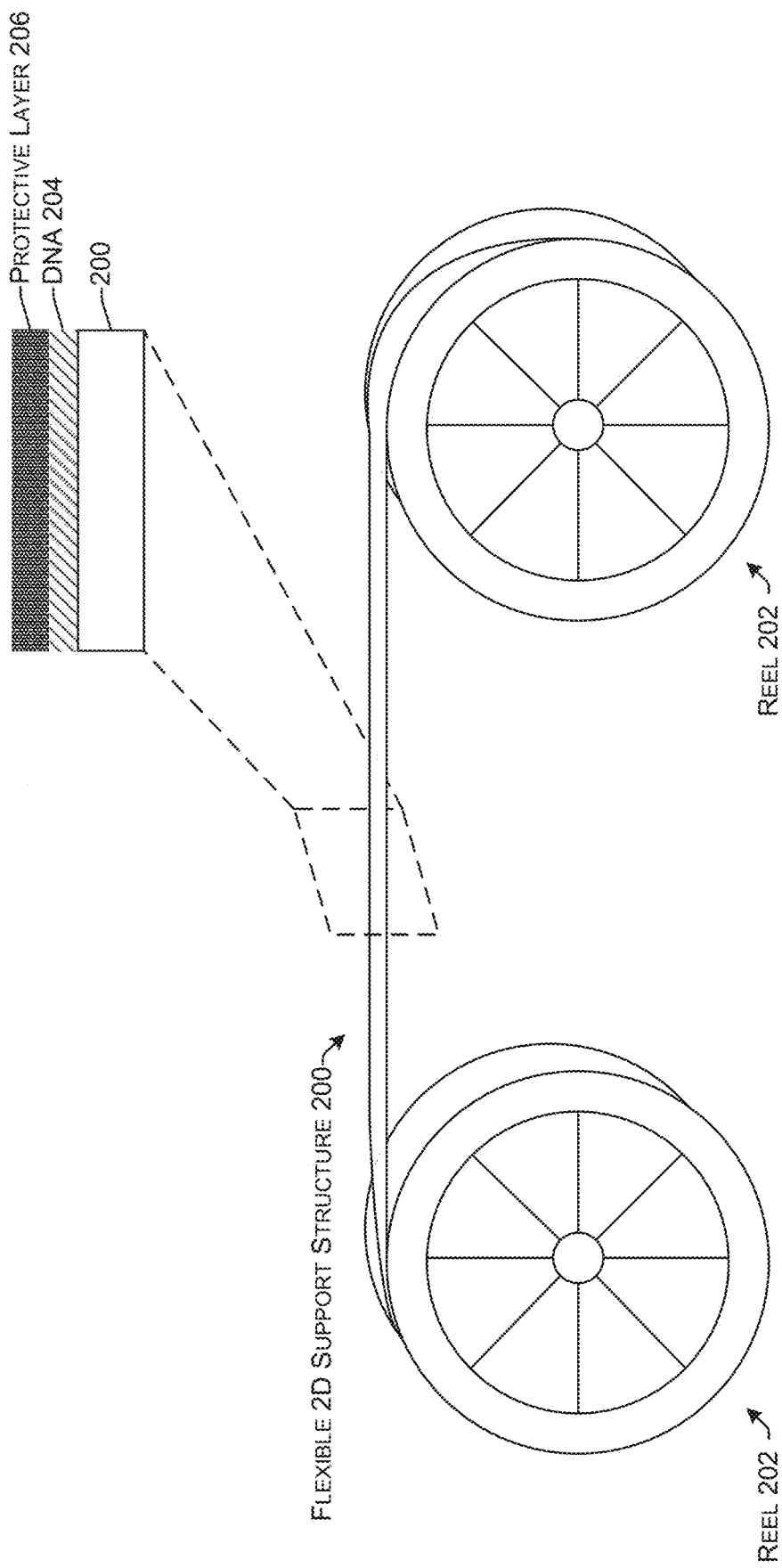
FIG. 2 is a diagram illustrating DNA stored on a flat, flexible 2D support structure in a reel-to-reel configuration.

FIG. 2 shows an illustrative implementation of a flexible 2D support structure 200 stored on one or more reels 202. The flexible 2D support structure 200 is made of a thin flexible material such as a thin sheet of glass, a metal film, or a plastic. DNA 204 may be deposited on the surface of the flexible 2D support structure 200 using any of the techniques described herein. Thus, one or more DNA layers 204 may be adsorbed to the surface of the flexible 2D support structure 200 and encapsulated with a protective layer 206. Additionally, DNA may be adhered to both the top and bottom surface of the flexible 2D support structure 200.

The flexible 2D support structure 200 has a tape-like shape with its length being many times its width. The flexible 2D support structure 200 may be wound around a reel 202 for compact storage. When unwound from the reel 202, a portion of the flexible 2D support structure 200 may be substantially flat. It is this substantially flat portion of the flexible 2D support structure 200 (not portions wound around a reel 202) that is used for adhering the DNA and accessing stored DNA.

In this implementation, the flexible 2D support structure 200 may function similar to magnetic tape used for storing digital information. The physical configuration of the flexible 2D support structure 200 and the one or more reels 202 may be similar to any of the physical formats used for magnetic tape data storage. For example, the flexible 2D support structure 200 may be stored on a single reel 202 and accessed using a reel-to-reel system that suspends the flexible 2D support structure 200 between two reels 202. Cartridges and/or cassettes using one or more reels 202 may also be used to hold the flexible 2D support structure 200.

One way to apply the protective layer 206 to the flexible 2D support structure 200 is to place the entire flexible 2D support structure 200 into a silica bath to create a thin layer of silica that coats all sides of the flexible 2D support structure 200. Alternatively, the flexible 2D support structure 200 could be passed through a silica bath, PVD, CVD, or other coating method that applies the protective layer 206 to a portion of the flexible 2D support structure 200 as it moves through the bath or deposition chamber. A thin coating of silica (e.g. about 10 nm) is sufficiently flexible so that it can flex with the flexible 2D support structure 200 as it is wound around a reel 202.

The reel(s) 202 may be operated by a computer-controlled motor using techniques similar to those used with magnetic tape data storage for automatically accessing a specified location along the length of the flexible 2D support structure 200. This provides controlled access to any location along the length of the flexible 2D support structure 200. DNA stored at that location may be selectively retrieved thereby providing addressability.

Figure 3:
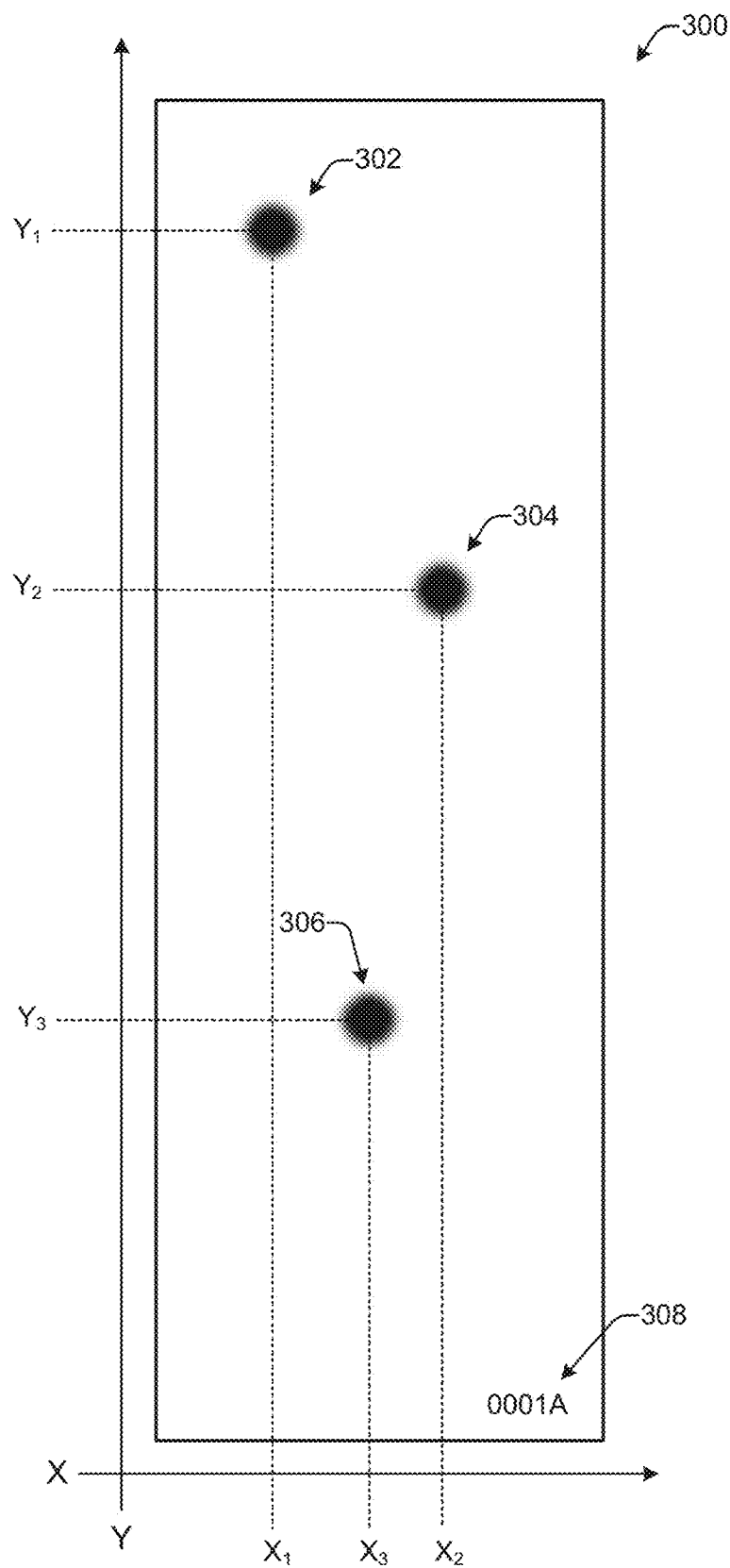
FIG. 3 is a diagram of a 2D support structure, such as a microscope slide, having DNA deposited at multiple discrete locations on a surface of the 2D support structure.

FIG. 3 shows an illustrative 2D support structure 300 with DNA located at multiple, geometrically-addressable positions. In this example, there are three groupings of DNA 302, 304, at 306. However, there may be many hundreds or thousands of separate groupings of DNA on the 2D support structure 300.

In one implementation, the 2D support structure 300 may be a commercially available microscope slide. The microscope slide may be made of glass and may have a rectangular shape with a flat surface of 75×24 mm and a thickness of about one mm. There is a large variety of robotic slide handling equipment that provides many options for automatically manipulating microscope slides. Thus, existing systems for automatically handling microscope slides may be readily adapted to use for DNA storage. However, as described above, other types of support structures besides microscope slides and other types of material besides glass may be used.

The 2D support structure 300 may be prepared by cleaning and functionalization as described above. DNA may be applied to specific locations on the surface of the 2D support structure 300 by use of a pipette to deposit a small volume of DNA that is suspended in water or a buffered solution. The DNA may be in a solution of annealing buffer (e.g., at a concentration of 50 µg/mL). The annealing buffer may be any standard buffering solution for DNA such as 400 mM Tris-HCl, 500 mM NaCl, and 100 mM $MgCl_2$. The DNA molecules in the solution may have a length of about 100-300 bp, 120-180 bp or approximately 150 bp.

The pipette may be controlled by an automated pipetting system that uses robotics including microfluidics to perform automated liquid handling. The automated pipetting system may be capable of placing a small volume of liquid at a designated point upon the surface of the 2D support structure 300. For example, a dilute solution of DNA with a concentration of approximately one ng per µL may be applied to a glass surface and allowed to dry thereby creating one of the DNA groupings 302, 204, or 306.

Other techniques besides pipetting may be used to deposit DNA onto the 2D support structure 300. For example, any technique used for DNA microarray printing may be adapted to place DNA at specific, predetermined locations on a microscope slide or other support material. Microarray fabrication techniques including printing with fine-pointed pins onto glass slides, photolithography using pre-made masks, photolithography using dynamic micromirror devices, electrospray deposition, DNA droplet printing, and ink-jet printing.

Regardless of the type of support structure or technique for placing DNA, multiple groupings of DNA may be placed at specific, geometrically-addressable locations on a flat surface of the 2D support structure 300. Each DNA grouping 302, 304 and 306 is deposited at a separate, predetermined location. The location may be indicated by a horizontal and a vertical offset along an x-axis and along a y-axis. The x- and y-axes may be defined as the edges of the 2D support structure 300. If implemented in a tape like format as illustrated in FIG. 2, the y-axis may be represented by the distance along the tape from one of the ends. The distance along the horizontal and vertical offset may be measured relative to a corner of the 2D support structure 300 or relative to another reference point. In this illustrative example, a first grouping of DNA 302 is located at a position having the coordinates $X_1$, $Y_1$, a second grouping of DNA 304 is located at the coordinates $X_2$, $Y_2$ and the third grouping of DNA 306 is located at the coordinates $X_3$, $Y_3$. The X and Y coordinates may be indicated by any suitable unit of length such as millimeters.

The contents of a specific DNA grouping, such as DNA grouping 302, together with the horizontal and vertical offset (e.g., $X_1$, $Y_1$) and identification of the 2D support structure 300 such as a substrate number 308 may be recorded in conventional electronic media to provide a lookup record for the DNA grouping 302. The contents of the DNA grouping 302 may be identities of specific DNA molecules contained within the DNA grouping 302 and/or information encoded by those DNA molecules such as the name of a digital file. Thus, this DNA grouping 302 can be later accessed by locating the 2D support structure 300 (e.g., by having automated slide handling equipment retrieve a specified slide from a storage rack) and then applying an etching solution such as hydrogen fluoride to dissolve the protective silica layer. The DNA grouping 302 may be resuspended in aqueous solution and removed from the surface of the 2D support structure 300. Microfluidics or other type of automated liquid handling equipment may be used to both apply etching solution at the specified x- and y-coordinates, to resuspended DNA, and to remove the liquid containing the resuspended DNA.

ILLUSTRATIVE PROCESS

For ease of understanding, the process discussed in this disclosure is delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process or an alternate process. Moreover, it is also possible that one or more of the provided operations is modified or omitted.

Figure 4:
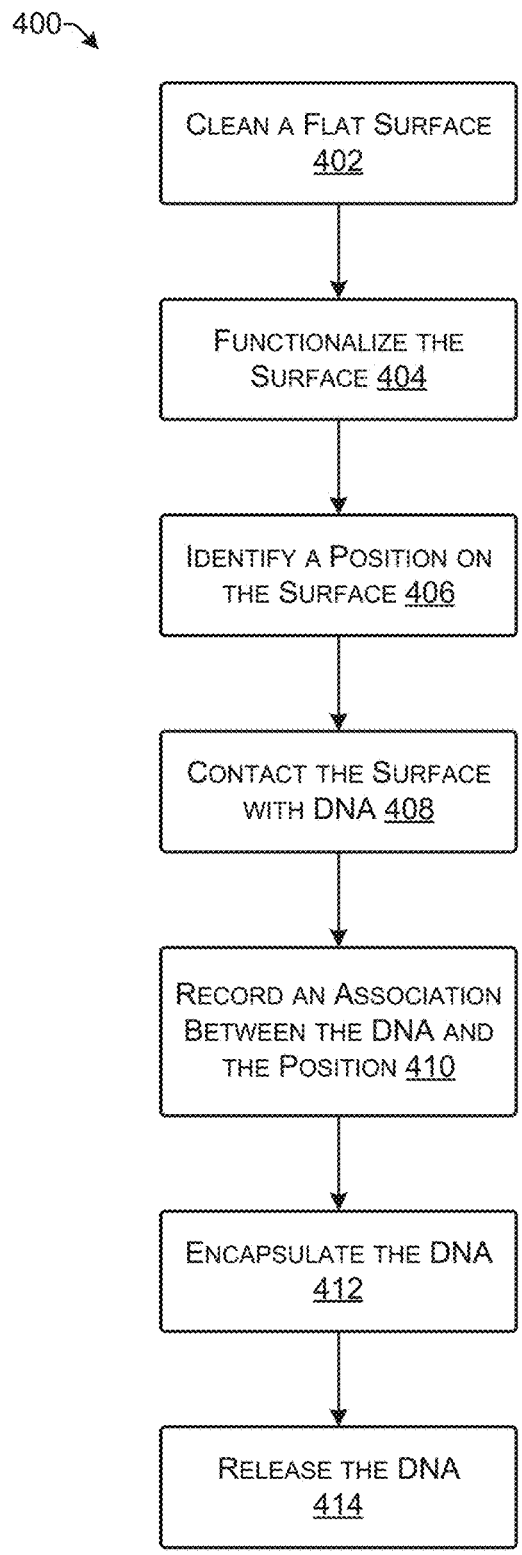
FIG. 4 is flow diagram of a process for storing DNA on a 2D support structure.

FIG. 4 shows process 400 for encapsulating DNA at a specific, identifiable location on the surface of a 2D support material. The DNA may be used for storing digital information. Encapsulation in a protective material may provide for stable, long-term storage, and placement on a flat 2D support material at a known location provides for addressability.

At 402, a substantially flat surface is cleaned. The flat surface may be made of glass, a metal foil (e.g., aluminum, copper, or tin), plastic, or another material. Cleaning removes organic material and other contaminants from the surface. The cleaning may be performed by a chemical solution that is corrosive, oxidizing, or both. One chemical solution that is suitable for cleaning glass and aluminum surfaces is piranha solution.

At 404, the surface of the flat 2D support material is functionalized. The functionalization places a positive charge onto the surface. DNA may be adsorbed to the surface by electrostatic forces due to the negative charge of DNA strands. The functionalization may be provided by contacting the surface with an amine bearing silane linker. One suitable amine bearing silane linker is TMAPS.

At 406, a position on the surface of the flat 2D support material is identified. The position on the surface may be identified by a vertical and horizontal offset from a reference point. For example, a corner of the surface may be the reference point and the location may be identified by a distance (e.g., in mm) from the reference point along an x-axis and a y-axis. Other geometric reference schemata are also possible. For example, if the surface of the 2D support material is generally circular, the position may be identified by an angle and a distance from the center of the surface.

At 408, the substantially flat surface is contacted with the DNA. The DNA is placed at the position on the surface identified in 406. The contacting may be performed by any technique suitable for placing DNA at a specific position on a flat surface. For example, the DNA may be placed on the surface by pipetting, microarray printing, electrospray deposition or other technique. The DNA may encode digital information such as all or a portion of a computer file. The DNA may be provided in an aqueous solution such as an annealing buffer at a concentration of, for example, around 20, 30, 40, 50, 60, 70, 80, 90, or 100 µg/mL.

At 410, an association between the DNA and the position is recorded. Creating a linkage between specific groupings of DNA and physical location provides addressability lacking in other techniques for DNA storage. The position may be stored in association with an indication of the contents of the DNA. This association may be stored, for example, in a look-up table in conventional digital storage media. In a system in which there are multiple separate pieces of 2D support material (e.g., multiple glass slides or multiple reels of aluminum foil tape) the association may also include an indicator of the specific piece of 2D support material such as a slide or cassette number.

At 412, the DNA is encapsulated under a protective layer. The protective layer may be a thin layer of silica, gold, aluminum oxide or titanium oxide that protects the DNA from degradation by oxygen, water, and other substances such as reactive oxygen species (ROS). ROS are chemically reactive chemical species containing oxygen. Examples include peroxides, superoxide, hydroxyl radical, and singlet oxygen. A protective layer of silica may be formed around the DNA by contacting the DNA with a tetra alkoxysilane. The tetra alkoxysilane may be tetramethyl orthosilicate, tetraethyl orthosilicate (TEOS), tetrapropyl orthosilicate, tetrabutyl orthosilicate, tetrapentyl orthosilicate, or mixtures thereof. Contacting the surface with the tetra alkoxysilane may be performed for a prolonged period of time such as three hours, 12 hours, 24 hours, 48 hours, 72 hours, 96 hours, or more. Longer periods of contact may result in a thicker and more dense silica shell.

Following encapsulation of the DNA, and all other groupings of DNA on the same 2D support material, the 2D support material with the encapsulated DNA may be stored for a short or long period of time. Longevity of the DNA may be further enhanced by favorable storage conditions such as cool temperatures and low humidity (e.g., 9° C. and 20% RH). When encased in silica and stored under favorable conditions, the DNA may be preserved without significant degradation for hundreds, thousands, or potentially millions of years.

At 414, the DNA is released from the encapsulation and from the substantially flat surface of the 2D support material. The protective layer may be contacted with an etching buffer that dissolves the protective layer. Silica dissolves rapidly in fluoride-containing solutions (forming $SiF_6^{2-}$). Thus, an etching buffer containing fluoride may be used to dissolve protective layers formed from silica. The compatibility of dilute etching solutions and DNA (DNA is not affected by $F^-$ ions) has previously been shown. The etching buffer may be a mixture of buffering agents such as ammonium fluoride ($NH_4F$) and hydrofluoric acid (HF). In an implementation, the etching buffer may be prepared by dissolving 0.23 g of ammonium hydrogen difluoride ($NH_4FHF$, puriss, Sigma-Aldrich, catalog number 30101) in 5 mL of $H_2O$ and 0.19 g of $NH_4F$ (puriss, Sigma-Aldrich, catalog number 30101) in 5 mL of $H_2O$ then mixing the two solutions together. Metals such as gold and aluminium oxide can be etched with potassium cyanide (KCN). Protectively layers formed from titanium oxide may be etched with hydrogen fluoride (HF) solutions.

The etching solution is applied to the identified location on the surface of the 2D support material from 406 that contains the DNA of interest. Microfluidics or another controlled fluid-delivery system may be used to deliver the etching solution to a specific location. The etching solution dissolves the protective layer and the DNA may be removed from the surface of the 2D support material. If the backing is made of a similar material as the protective layer (e.g., silica encapsulation on a glass backing), the etching solution may make a hole in the backing. The 2D support material, with the hole, may be returned to storage with the other DNA groupings undisturbed. Holes may also be punched in the 2D support material with a hole punch to remove a DNA grouping for processing physically separate from the remainder of the 2D support material. Many thin support materials may be mechanically punctured with a hole punch to remove one or more DNA groupings without disturbing the rest of the 2D support material.

After removal of the protective layer, the DNA may be contacted with a release solution. The release solution may be formulated as a buffered aqueous solution that contains polyanionic molecules. The release solution may be made by diluting 40 mg of poly(acrylic acid) sodium (PAS) in 50 mL of ultrapure water to a concentration of 0.8 mg/mL and mixing that with sodium chloride diluted in ultrapure water until saturation at room temperature in a ratio of PAS:NaCl=20:80. PAS is a polyanionic molecule that displaces the DNA from the positively-charged functionalized surface. As used herein, "ultrapure water" refers to water having a purity such that resistivity is 18.2 MΩ·cm at 25° C. or "type 1" water as specified in ISO (International Organization for Standards) 3696. One source of ultrapure water is Milli-Q™ water available from Millipore Corporation.

Once released and purified to remove remnants of the protective layer, salts, and other compounds, "clean" DNA may be amplified by polymerase chain reaction (PCR) which exponentially increases the quantity of DNA. The sequence of the DNA can be read by an oligonucleotide synthesizer. If the sequence of the DNA encodes digital information, that sequence may be decoded and the digital information recovered.

EXAMPLES

Figure 5:
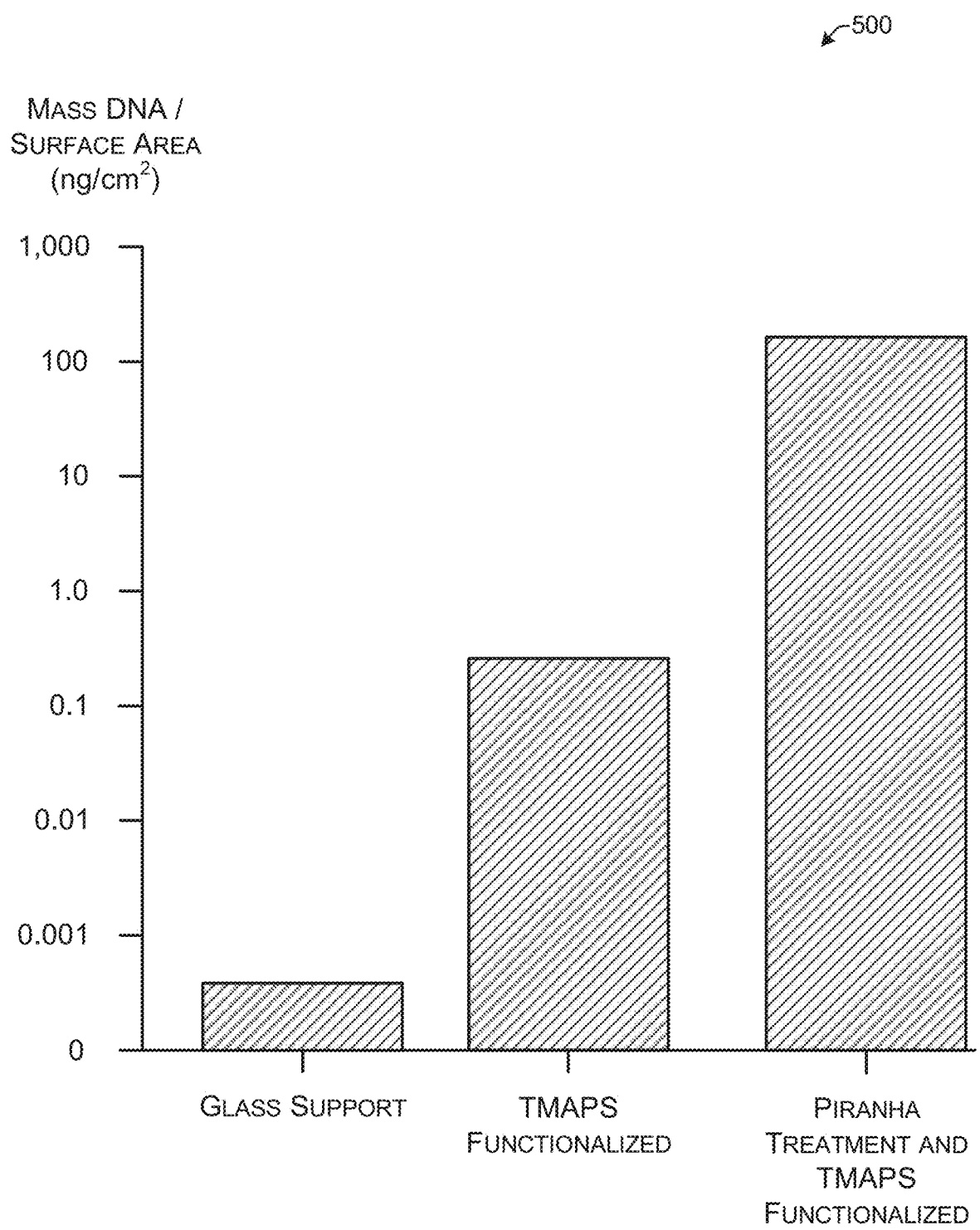
FIG. 5 is a bar chart showing the effects of surface treatments on the adsorption of DNA to a flat glass surface.

FIG. 5 is a bar chart 500 showing DNA absorption on glass slides with three different surface treatments. The amount of DNA absorption is shown on the vertical axis in logarithmic scale as nanograms of DNA per square centimeter. On an untreated glass surface, DNA was detected at a very low level of $3.84 \times 10^{-4}$ ng/cm². TMAPS functionalization to add a positively charged layer to the glass slide resulted in a small level of DNA absorption (0.258 ng/cm²). However, a much higher level of DNA deposition was achieved when Nano-Strip® solution was used to clean the glass before functionalization with TMAPS. Without being bound by theory, it is believed that cleaning the surface with a piranha solution leads to stronger adherence of the TMAPS to the glass surface and more positively charged functional groups to bind the DNA. Functionalizing a glass surface with TMAPS following cleaning with a piranha solution achieved DNA loading of about 165 ng/cm². The loading density was calculated by quantifying the amount of DNA in solution using qPCR and dividing by the surface area of the glass slide. This loading density corresponds to a theoretical storage density of approximately 6.7 Terabytes per square centimeter.

Figure 6:
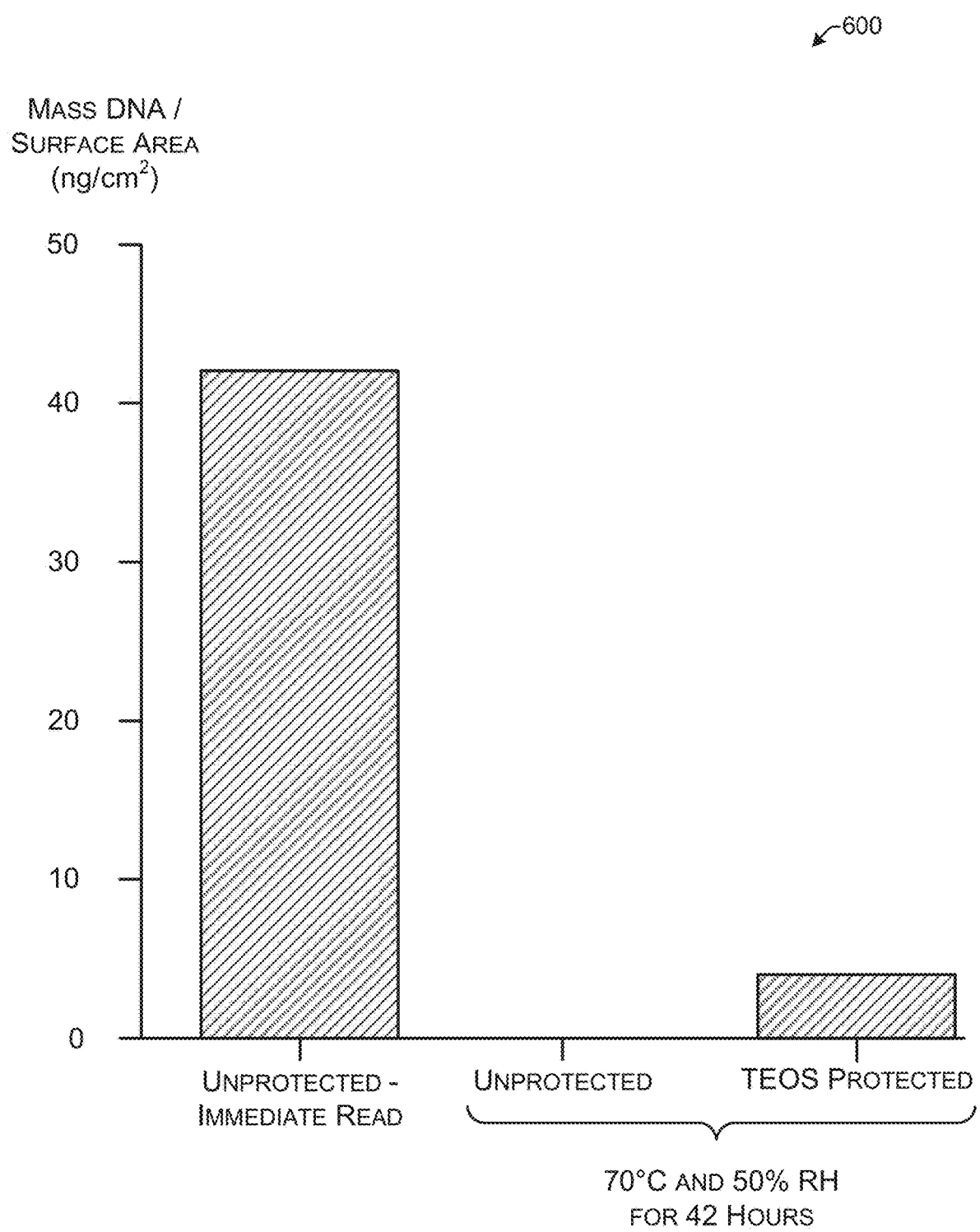
FIG. 6 is a bar chart comparing the surface density of DNA on a glass slide prior to storage and after storage at 70° C. and 50% RH for 42 hours with and without a protective silica layer.

FIG. 6 is a bar chart 600 comparing the amount of DNA present on a glass slide prior to storage with the amount of DNA remaining after incubation for 42 hours at 70° C. and 50% RH. This simulates the amount of thermal stress the DNA would experience stored at room temperature for approximately 100 years. The samples stored at high heat and high humidity are an unprotected DNA sample and a DNA sample protected by silica encapsulation. The amount of DNA absorption is shown on the vertical axis as nanograms of DNA per square centimeter. For each of the three samples, glass slides treated with piranha solution and functionalized with TMAPS. Equal quantities of DNA were initially adsorbed to all of the slides. The "unprotected—immediate read" slide was not subject to high heat or high humidity or prolonged storage. The loading density of DNA for this sample was measured shortly after the DNA was deposited. The "unprotected" slide received no further treatment beyond functionalization of the glass. The "TEOS protected" slide was encapsulated by growing a protective layer of silica around the DNA. The silica encapsulation was performed by placing the slides in a TEOS bath (≥99.0%, Aldrich, cat. no. 86578) with shaking.

Figure 7:
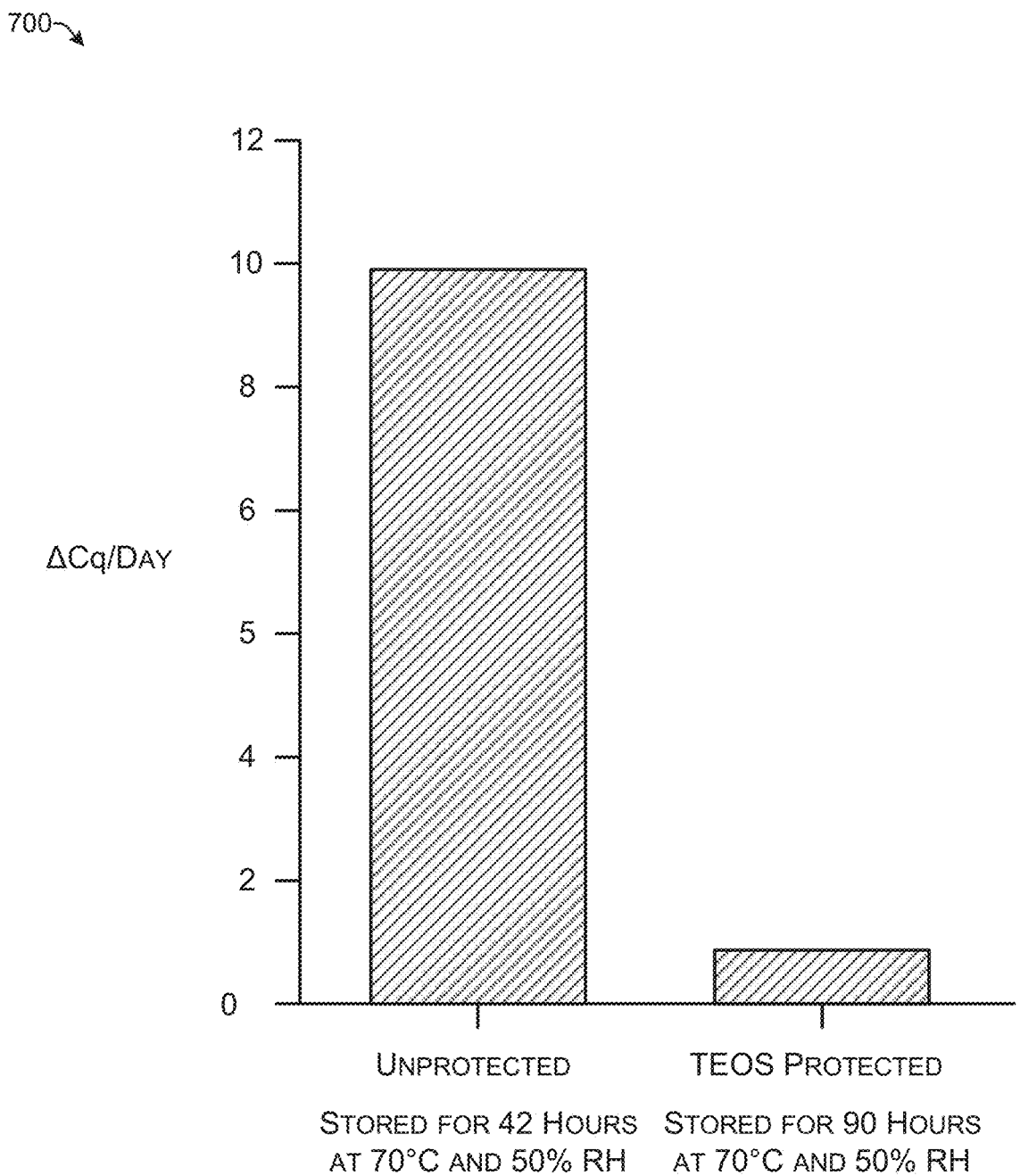
FIG. 7 is a bar chart comparing the amount of DNA as measured by quantitative PCR cycles after storage at 70° C. and 50% RH. The unprotected sample was stored for 42 hours and the sample with a protective silica layer was stored for 90 hours.

The advantages of protection with the silica layer are apparent in this comparison. The DNA loading for the unprotected—immediate read sample was 42.1 ng/cm². Almost all of the DNA on the unprotected slide degraded; only $6.24 \times 10^{-5}$ ng/cm² remained. However, 4.00 ng/cm² of DNA remained on the slide protected with TEOS FIG. 7 is a bar chart 700 showing a comparison of DNA stability measured by change in Cq values (ΔCq). The vertical axis shows the quantitative PCR (qPCR) cycle difference per day. qPCR uses the linearity of DNA amplification to determine absolute or relative quantities of DNA in a sample. By using a fluorescent reporter in the reaction, it is possible to measure DNA generation in the qPCR assay as the PCR reaction proceeds in real time. The number of PCR cycles at which the fluorescence exceeds a detection threshold and becomes measurable is called the quantification cycle (Cq). A single cycle of PCR (assuming 100% efficiency) results in a doubling of the amount of DNA, so an increase of one in a Cq value indicates a halving of the DNA amount. Starting samples that include a larger amount of DNA reach the detection threshold with fewer PCR cycles than samples with a smaller amount of DNA. Thus, Cq values are inversely proportional to the amount of target DNA in the sample.

Both the unprotected sample and the sample protected by TEOS encapsulation were subjected to high heat and high humidity (70° C. with 50% RH) to simulated extended aging. Over a 42-hour testing period, the unprotected sample lost about 10 PCR cycles per day indicating that about 99.9% of the DNA was degraded in one day. TEOS encapsulation provided signification protection; this sample was stored for 90 hours but the ΔCq per day was only about 1 which corresponds to about 50% of the DNA remaining.

ILLUSTRATIVE EMBODIMENTS

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method of stably storing deoxyribose nucleic acid (DNA) in an addressable configuration on a two-dimensional (2D) support structure, the method comprising: cleaning a substantially flat glass surface with a piranha solution; functionalizing the glass surface with an amine bearing silane linker; identifying a position on the glass surface; placing the DNA on the glass surface at the position; recording an association between the DNA and the position; and forming a silica layer around the DNA by contacting the DNA with tetraethyl orthosilicate (TEOS).

Clause 2. A method of stably storing DNA comprising: obtaining a substantially flat surface that is functionalized with a positive charge; contacting the substantially flat surface with the DNA; and encapsulating the DNA on the substantially flat surface by forming a protective layer over the DNA on the substantially flat surface.

Clause 3. The method of clause 2, further comprising cleaning organic material from the substantially flat surface.

Clause 4. The method of clause 3, wherein the cleaning is performed by contacting the substantially flat surface with a solution that is corrosive and oxidizing.

Clause 5. The method of any of clauses 2-4, wherein the substantially flat surface is glass, metal foil, or a plastic formed from one or more polymers.

Clause 6. The method of any of clauses 2-5, wherein functionalization is performed by contacting the substantially flat surface with an amine bearing silane linker.

Clause 7. The method of any of clauses 2-6, wherein the contacting the substantially flat surface with DNA is performed by microarray printing or spray deposition.

Clause 8. The method of any of clauses 2-7, wherein the protective layer comprises silica, titanium oxide, aluminum oxide, or gold.

Clause 9. The method of any of clauses 2-8, further comprising releasing the DNA from the substantially flat surface by: identifying a location on the substantially flat surface associated with the DNA; and contacting the protective layer at the location with (i) an etching buffer that dissolves the protective layer and with (ii) a polyanionic molecule.

Clause 10. An article of manufacture comprising: a 2D support structure; first DNA located at a first position on the 2D support structure; second DNA located at a second position on the 2D support structure; and a silica coating encapsulating the first DNA and the second DNA on the 2D support structure.

Clause 11. The article of manufacture of clause 10, wherein the 2D support structure comprises glass.

Clause 12. The article of manufacture of clause 11, further comprising N-trimethoxysilylpropyl-N,N,N-trimethylammonium chloride (TMAPS) functionalization on the glass.

Clause 13. The article of manufacture of any of clauses 10-12, wherein the 2D support structure comprises a metal foil.

Clause 14. The article of manufacture of clause 13, further comprising at least one reel, wherein at least a portion of the metal foil is wound around the reel.

Clause 15. The article of manufacture of any of clauses 10-14, wherein the first DNA encodes a first set of digital information and the second DNA encodes a second set of digital information.

Clause 16. The article of manufacture of any of clauses 10-15, wherein the first position is at a first, predetermined x-coordinate and y-coordinate position on the 2D support structure and the second position is at a second, predetermined x-coordinate and y-coordinate position on the 2D support structure.

Clause 17. The article of manufacture of clause 16, wherein contact by a fluoride etching solution with the silica coating at the first, predetermined x-coordinate and y-coordinate position releases the first DNA and contact by an aqueous solution without fluoride does not release the first DNA.

Clause 18. The article of manufacture of any of clauses 10-17, wherein the silica coating comprises one or more tetra alkoxysilanes.

Clause 19. The article of manufacture of any of clauses 10-18, further comprising a polycationic molecule layer and a third DNA, wherein the first DNA and the second DNA are between the 2D support structure and the polycationic molecule layer and the third DNA is between the polycationic molecule layer and the silica coating.

Clause 20. The article of manufacture of any of clauses 10-19, wherein a density of all DNA on the 2D support structure is at least 150 ng/cm$^2$.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention (especially in the context of the following claims) are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. As used herein, "approximately" or "about" or similar referents denote a range of ±10% of the stated value.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications (collectively "references") throughout this specification. Each of the cited references is individually incorporated herein by reference for its particular cited teachings as well as for all that they disclose.

The invention claimed is:

1. A method of stably storing DNA comprising:
   obtaining a flat surface that is functionalized with a positive charge;
   contacting the flat surface with a layer of DNA;
   encapsulating the layer of DNA on the flat surface by forming a protective layer over the layer of DNA on the flat surface;
   identifying a location on the flat surface associated with a specific subset of the DNA contained in the layer of DNA; and
   releasing the specific subset of the DNA from the flat surface by contacting the protective layer at the location with (i) an etching buffer that dissolves the protective layer and with (ii) a polyanionic molecule.

2. The method of claim 1, wherein the flat surface is glass, metal foil, or a plastic formed from one or more polymers.

3. The method of claim 1, wherein the contacting the flat surface with the layer of DNA is performed by microarray printing or spray deposition.

4. The method of claim 1, wherein the protective layer comprises silica, titanium oxide, aluminum oxide, or gold.

5. The method of claim 1, wherein the flat surface has a radius of curvature that is less than 1 meter.

6. The method of claim 1, wherein the protective layer encapsulates the layer of DNA without fully surrounding the flat surface.

7. The method of claim 1, further comprising applying the etching buffer to the location on the flat surface by microfluidics.

8. The method of claim 1, wherein the polyanionic molecule displaces the DNA from the flat surface that is functionalized.

9. The method of claim 1, further comprising cleaning organic material from the flat surface.

10. The method of claim 9, wherein the cleaning is performed by contacting the flat surface with a solution that is corrosive and oxidizing.

11. The method of claim 1, wherein functionalization is performed by contacting the flat surface with an amine bearing silane linker.

12. The method of claim 11, wherein the functionalization is performed by contacting the flat surface with N-trimethoxysilylpropyl-N,N,N-trimethylammonium chloride (TMAPS) and the protective layer comprises tetraethyl orthosilicate (TEOS).

13. The method of claim 1, further comprising:
   creating a record that includes information encoded by the DNA or identities of specific DNA molecules included in the DNA and a location on the flat surface.

14. The method of claim 13, wherein the location on the flat surface comprises an indication a horizontal offset and a vertical offset.

15. The method of claim 1, further comprising:
   contacting the layer of DNA with a polycationic molecule;
   contacting the flat surface with a second layer of DNA such that the second layer of DNA is deposited on a positively charged layer formed from the polycationic molecule;
   wherein the encapsulating further comprises forming the protective layer over the second layer of DNA on the flat surface; and
   wherein releasing the specific subset of the DNA from the flat surface further comprises releasing a second specific subset of the DNA from the second layer of DNA.

16. The method of claim 15, wherein the polycationic molecule comprises one or more of polyethyleneimine (PEI), poly-l-lysine (PLL), diethylaminoethyl-dextran (DEAE-dextran), or poly(amidoamine) (PAMAM) dendrimers.

17. A method of stably storing DNA comprising:
   obtaining a flat surface that is functionalized with a positive charge;
   contacting the flat surface with a first layer of DNA;
   contacting the first layer of DNA with a polycationic molecule;
   contacting the flat surface with a second layer of DNA such that the second layer of DNA is deposited on a positively charged layer formed from the polycationic molecule;
   encapsulating the first layer of DNA and the second layer of DNA on the flat surface by forming a protective layer over the first layer of DNA and the second layer of DNA on the flat surface;
   identifying a location on the flat surface associated with a first specific subset of the DNA contained in the first layer of DNA or a second specific subset of the DNA contained in the second layer of DNA; and
   releasing the first specific subset of the DNA and the second specific subset of the DNA from the flat surface by contacting the protective layer at the location with (i) an etching buffer that dissolves the protective layer and with (ii) a polyanionic molecule.

18. The method of claim 17, wherein the first specific subset of the DNA encodes a first set of digital information and the second specific subset of the DNA encodes a second set of digital information.

19. The method of claim 17, wherein the specific location is at a predetermined x-coordinate and y-coordinate position on the flat surface.

20. The method of claim 17, wherein the releasing the first specific subset of the DNA and the second specific subset of the DNA does not release other DNA in the first layer of DNA or the second layer of DNA.

\* \* \* \* \*